United States Patent [19]

DiPace et al.

[11] Patent Number: 5,418,944
[45] Date of Patent: May 23, 1995

[54] KNOWLEDGE-BASED MOLECULAR RETRIEVAL SYSTEM AND METHOD USING A HIERARCHY OF MOLECULAR STRUCTURES IN THE KNOWLEDGE BASE

[75] Inventors: Luigi DiPace, Pomezia; Filippo Fabrocini, Rome, both of Italy

[73] Assignee: International Business Machines Corporation, Armonk, N.Y.

[21] Appl. No.: 824,629

[22] Filed: Jan. 23, 1992

[51] Int. Cl.$^6$ ............................................. G06F 15/40
[52] U.S. Cl. ................................. 395/600; 364/496; 364/DIG. 1; 364/223.4
[58] Field of Search ................... 364/496, 497, 499; 395/600

[56] References Cited

U.S. PATENT DOCUMENTS

| | | | |
|---|---|---|---|
| 4,642,762 | 2/1987 | Fisanick | 395/600 |
| 4,719,582 | 1/1988 | Ishida et al. | 364/498 |
| 4,811,217 | 3/1989 | Tokizane et al. | 395/800 |

OTHER PUBLICATIONS

Brugge et al., "Evolution of a Knowledge-Based System for Determining Structural Components of Proteins", *Expert Systems*, Aug. 1989, pp. 144-156.
Lathrop et al., "Ariadne: Pattern-Directed Inference and Hierarchical Abstraction in Protein Structure Recognition"; *Communications of the ACM*, Nov. 1987, pp. 909-921.
Lathrop et al., "Ariadne: Pattern-Directed Inference and Hierarchical Abstraction in Protein Structure Recognition", Communications of the ACM, vol. 30, No. 11, Nov. 1987.
Brugge et al., "Evolution of a Knowledge-Based System for Determining Structural Components of Proteins", Expert Systems, vol. 6, No. 3, Aug. 1989.
Pogue et al., "Searching and Clustering of Databases Using the ICL Distributed Array Processor", Parallel Computing, vol. 8, No. 1-3, Oct. 1988.
Ferrin et al., "The MIDAS Database System", J. Mol. Graphics, vol. 6, No. 1, Mar. 1988.

Primary Examiner—Thomas G. Black
Assistant Examiner—John C. Loomis
Attorney, Agent, or Firm—Robert B. Martin

[57] ABSTRACT

A molecular retrieval system and method answering to similarity queries for retrieving molecular structures, stored into a source database (22) and having a required similarity with an input structure, which can contain a set of property regions. A target database (23) stores the molecular structures described in hierarchical way and a knowledge base (24) stores well-known molecular fragments at different levels of description together with a set of physical and chemical properties associated to each fragment. A fragment recognizer (21) analyzes the fragments of the input structure to represent them in a hierarchical way. A query analyzer (25) analyzes the similarity queries and selects the appropriate level of molecular representation on the basis of the required similarity. Matching means (26, 27, 29), when called by the query analyzer (25), perform a matching of the representation of the input structure against the representations of the molecular structures stored into the target database (23) at the selected level of molecular representation.

6 Claims, 6 Drawing Sheets

$R_0$: (Polarity=Yes) & (3<Atoms<9)

$R_1$: (Hydrophobicity=Yes) & (30<Volume<70)

KNOWLEDGE-BASED MOLECULAR RETRIEVAL SYSTEM AND METHOD USING A HIERARCHY OF MOLECULAR STRUCTURES IN THE KNOWLEDGE BASE

The invention relates to the Computer Aided Molecular Design (CAMD) field and, more particularly, to those systems and methods that automatically allow the retrieval of molecules previously snored into a molecular database.

Specifically, the invention relates to a knowledge-based molecular retrieval system and method allowing queries for similarity in structure and properties which can be evaluated on whatever molecular substructure in whatever database. The invention makes use of a knowledge base of chemical and physical properties associated with the molecular database. Such a coupling between knowledge base and database allows to deal with non-trivial queries so as to end up in the retrieval of information inaccessible with standard techniques.

The molecular design process is generally considered a hard task involving hundreds of experiments needed to synthesize one optimal molecule. As it is obvious, therefore, chemical and pharmaceutical industries look forward to having new computer tools useful to assist the scientist in such a process. Molecular databases are, among other tools, one of the most widespread. A number of molecular databases are presently available on the market; such databases integrate large amounts of molecules collected from different experimentations. A frequent use of molecular databases consists in retrieving a set of target molecules in some aspect similar to an input one so as to allow the study of such a class of molecules without further experimentations.

Unfortunately, today's molecular retrieval systems allow the user only to perform a substructure search, i.e. a search for molecules containing a given substructure described in terms of atoms and connectivities. More recently, Molecular Design Limited has put on the market a retrieval system which allows a sort of query for molecular similarity. Yet, such similarity is simply based on the evaluation of common features (attributes with the same value) previously stored by human experts, for each molecule, in the database. In a real case, this is impracticable, because it would require that someone analyzes each of the molecules in the database and, for each of them, describes a number of features both of the molecules as a whole and of substructures of the molecule (all the conceivable ones) sufficient for satisfying any kind of query coming from the users.

More realistically, what happens is that only from 10 up to 20 features are associated with each of the molecules in the database. As a consequence, scientists have to study a set of complex queries to capture the subset of molecules to be searched in the database. However, in such a procedure, the major burden for abstraction and retrieval is put on the user. Yet, even in this case, too often the result of the query is a very large number of molecules, most of which are not useful for the purposes of the user. On the other side, other molecules useful to the scientist in order to carry out his/her activity are not captured by the query and, therefore, ignored by the system.

The invention as claimed is intended to remedy these drawbacks. It solves the problem of scientists who require more powerful molecular retrieval tools, allowing them to make queries in a selective way so as to easily reflect molecular similarity and effectively use the information stored into the database.

Another advantage offered by the invention is that the preliminary analysis of molecules and the storing of similarity features into the databases is not needed.

The system and method allow to satisfy a number of queries concerning:

1. molecules structurally similar to an input one;
2. molecules including a property region which verifies a user defined combination of chemical and physical properties;
3. molecules matching a user defined model conceived as a general molecular structure which relates property regions and molecular fragments.

Once selected a set of molecules, it is also possible to perform further operations on them such as, for instance, making the system select the pairs of molecules with minimal structural difference and maximal activity difference, where activity is a value related to a given property (a very useful mechanism when dealing with the Structure Activity Relationship problem in order to locate those fragments responsible for a major increase of the desired activity).

One way of carrying out the invention is described in detail below with reference to the drawings which illustrate a specific embodiment, in which.

Table 1 is a list of properties used to describe the residues appearing inside the corresponding knowledge-based dictionary.

Table 2 is a list of properties used to describe the functional groups appearing inside the corresponding knowledge-based dictionary.

Table 3 is a list of properties used to describe the atom types appearing inside the corresponding knowledge-based dictionary.

Table 4 is the description of the structural matching routine.

Table 5 is the description of the graph matching subroutine.

Table 6 is the description of the model matching routine.

Figure 1:
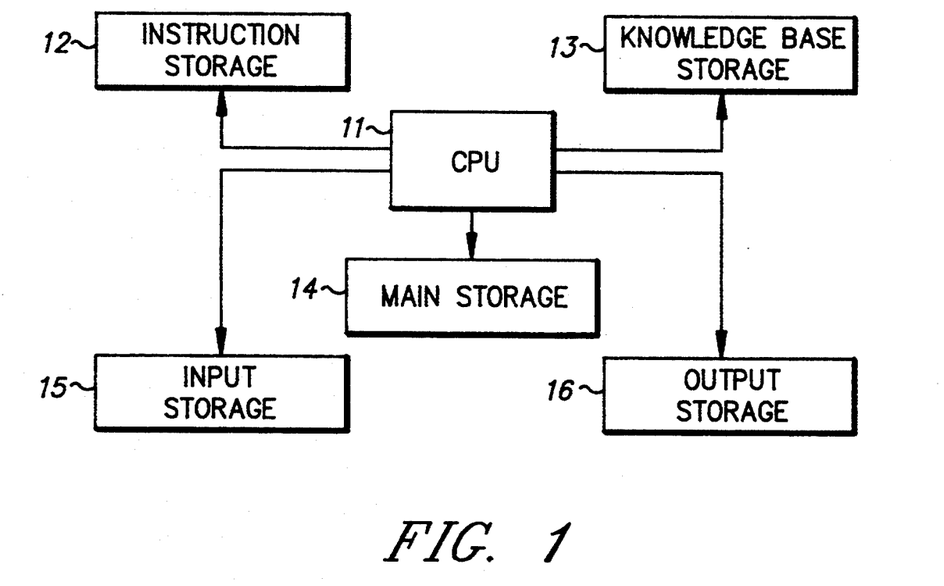
FIG. 1 is the hardware architecture of the retrieval system.

FIG. 1 shows the hardware of the molecular retrieval system which includes a CPU 11 of the general purpose type communicating with a storage 12 containing instructions that control its operation. Moreover, CPU 11 communicates with a storage 13 which contains a knowledge base where a number of chemical and physical properties is associated to a set of molecular fragments. Such fragments have been sorted into three dictionaries: a residue dictionary (the RS-dictionary), a functional group dictionary (the FG-dictionary) and an atom type dictionary (the AT-dictionary). Instruction storage 12 and knowledge base storage 13 may be of the read only storage or random access storage type. CPU 11 is also in communication with a main storage 14 of the random access storage type which is used for storing both the source database 22 and the target database 23 of FIG. 2. Input storage 15 is used to store the query entered from a source not shown in FIG. 1. Output storage 16 is used to memorize the results of the query.

Figure 2:
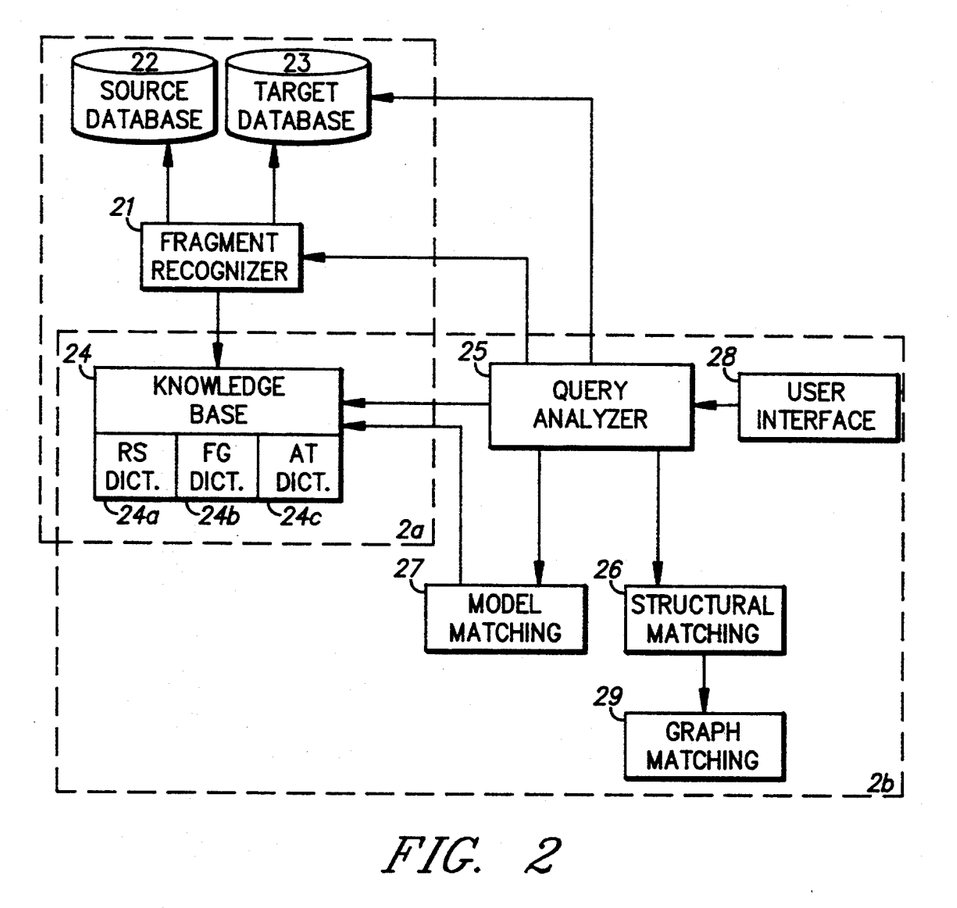
FIG. 2 is the software architecture of the retrieval system.

In the preferred embodiment of the invention a set of programs manipulates the input query so as to retrieve via similarity matching the searched molecules. The logical architecture of the system is illustrated in FIG. 2. Subsystem 2a made of modules 21, 22, 23, 24 will be firstly described. Subsystem 2a is used whenever a source database is associated with the retrieval system of the invention here described so as to generate a target database that will be the database effectively utilized during the retrieval process. The generation of the target database 23 must be viewed as a one time only reformulation process. A molecular fragment recognizer module 21 is in communication with both a source database 22 and a target database 23, both stored in a main storage 14. Module 21 also communicates with a knowledge base 24 stored in storage 13.

Molecular fragment recognizer 21 analyzes one or more source molecules to generate as output a hierarchical description of the source molecule (see below). Module 22 is a source database, i.e. the database to be associated with the information retrieval system. Molecules, in source database 22, are required to be described in terms of atoms and connectivities. Target database 23 is a database containing a hierarchically representation of each of the molecules stored into source database 22. Such a representation comprises three levels of description: the molecule described in terms of residues, the molecule described in terms of functional groups and the molecule described in terms of atomic entities. Knowledge base 24 is a dictionary of fragments having associated a number of well known chemical and physical properties. Specifically, the system makes use of a number of dictionaries corresponding to the number of representational levels above described (24a,24b,24c).

The operation of the subsystem 2a can be described as follows. Specifically, module 21 reads each of the molecules stored in terms of atomic entities into source database 22. Then, it makes use of RS-dictionary 24a and FG-dictionary 24b embedded into the knowledge base 24 to recognize the corresponding fragments inside the molecule. As a final result, a three level description of each molecule is generated and stored into target database 23. Whenever, during this process, fragments cannot be recognized neither as residues nor as functional groups, the formalization in terms of atomic entities is used to describe the molecule. Knowledge base 24 allows the system to accomplish such a step insofar as it allows the system to have a "perception" of the molecules as hierarchical entities with different representations of the molecule associated at each level of the hierarchy.

Figure 3:
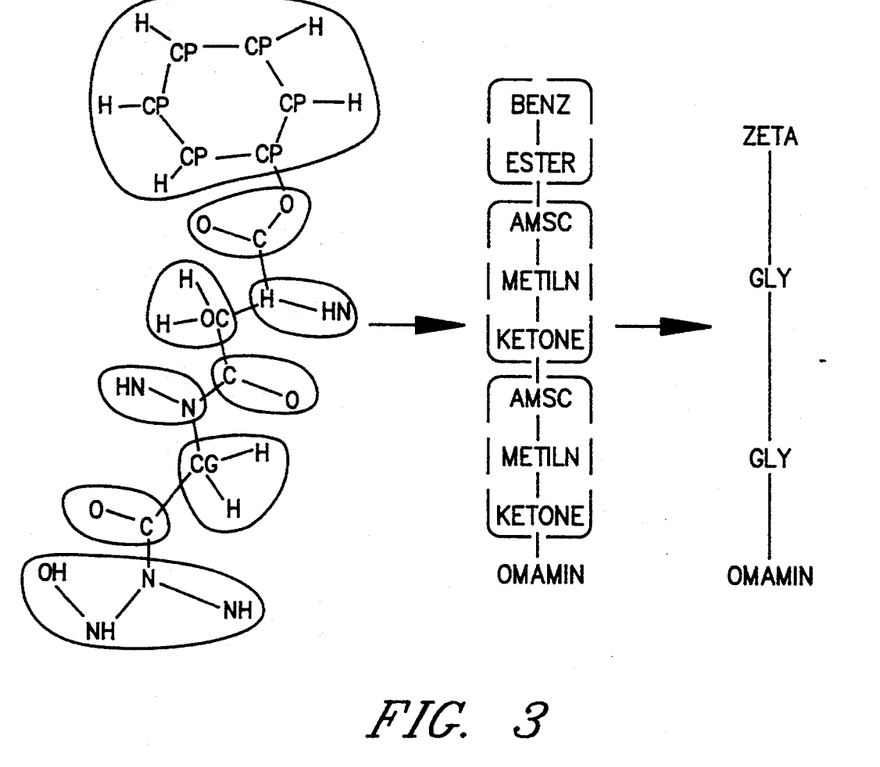
FIG. 3 shows the hierarchical representation used to describe the molecules.

FIG. 3 illustrates the hierarchical representation of a molecule obtained after this step. A molecule is described in terms of a graph in which nodes can be all residues, or all functional groups, or all atoms, and arcs stand for the connectivities between the said molecular fragments. Specifically, atomic entities are used to represent the molecule at the lower level (the AT-graph); in the following one, the molecule is represented in terms of larger fragments named functional groups such as, for instance, a carboxyl group (the FG-graph); at the next level up, the molecule is described in terms of residues such as, for instance, an amino-acid in a peptide (the RS-graph); finally, it is always possible to represent the molecule as a whole with some properties associated to the molecule such as, for instance, the molecular weight. FIG. 3, when read from left to right, illustrates firstly the AT-graph, then the FG-graph and, finally, the RS-graph; each circled region is in one-to-one correspondence to the circled region of the next hierarchical level. The hierarchical representation here described is an extension of the representation adopted by the MIDAS database system as presented by T. E. Ferrin et al. in the Journal of Molecular Graphics, vol. 6, March 1988, pp. 1-12.

Once target database 23 was generated, the molecular retrieval process starts when the user interface 28 receives the query to be processed from an input means not shown in FIG. 1 (keyboard, magnetic tape reader, diskette drive, etc.). User interface 28 is ill communication with a query analyzer 25 for the analysis of the query. Query analyzer 25, finally, is connected with a structural matching module 26 and a model matching module 27. Structural matching module 26 is also connected to a graph matching module 29. Query analyzer 25, finally, communicates with knowledge base 24, which is the only module of subsystem 2b also common to subsystem 2a.

Query analyzer 25 is the control module, which selects the appropriate subroutines according to the query type entered into the system. Knowledge base 24 has been partially illustrated during the description of the subsystem 2a. Specifically, module 24 comprises a number of dictionaries corresponding to the number of representational levels above described. Each dictionary is made of a set of fragments with a number of chemical and physical properties associated to each fragment. Thus, the hydroxyl group, for instance, appears into FG-dictionary 24b being described as a hydrophilic group with the property of being electron donor.

Table 1, Table 2 and Table 3, respectively, are the lists of properties presently being considered into modules 24c, 24b and 24a.

TABLE 1

*Hydrogen Bond
-Yes (donor, acceptor)
-No
*Nucleophilicity
-Yes (+, −)
-No
*Electrophilicity
-Yes (+, −)
-No
*Acidity
-Yes
-No
*Basicity
-Yes
-No

TABLE 2

*Polarity
-Yes (+, −)
-No
*Hydrophobicity
-Yes
-No
*Electron donor
-Yes
-No
*Electron acceptor
-Yes
-No TABLE 2-continued

*Volume
 -Evaluated by its
  subcomponents

TABLE 3

*Polarity
 -Yes (+, −)
 -No
*Hydrophobicity
 -Yes
 -No
*Volume
 -Evaluated by its subcomponents Structural matching module 26 and model matching module 27 are both used to test whether there are one or more molecules into target database 23 that satisfy the user query. Each of them is selected according to the query type entered by the user (see below). Graph matching module 29, finally, is a-graph matching subroutine used to match molecules described at any level of representation one onto the other.

The operation of the subsystem 2b made of modules 24, 25, 26, 27, 28, 29 is here described. Whenever a query is entered into module 28, it is processed in order to reformulate it in a standard form (the query statement). Such a step is necessary insofar as the user is normally supposed to enter the query in a graphical mode (see, for instance, FIG. 4). Then, the query statement is presented to query analyzer 25 in order to activate the appropriate routines for satisfying the user query. Firstly, it analyzes the input query to understand the query type. Query analyzer 25, according to the input query, will select a number of subroutines implemented to deal with the given query. Module 25 has been designed to deal with four query types. The operation of the retrieval system is described in connection with each query type.

Figure 6:
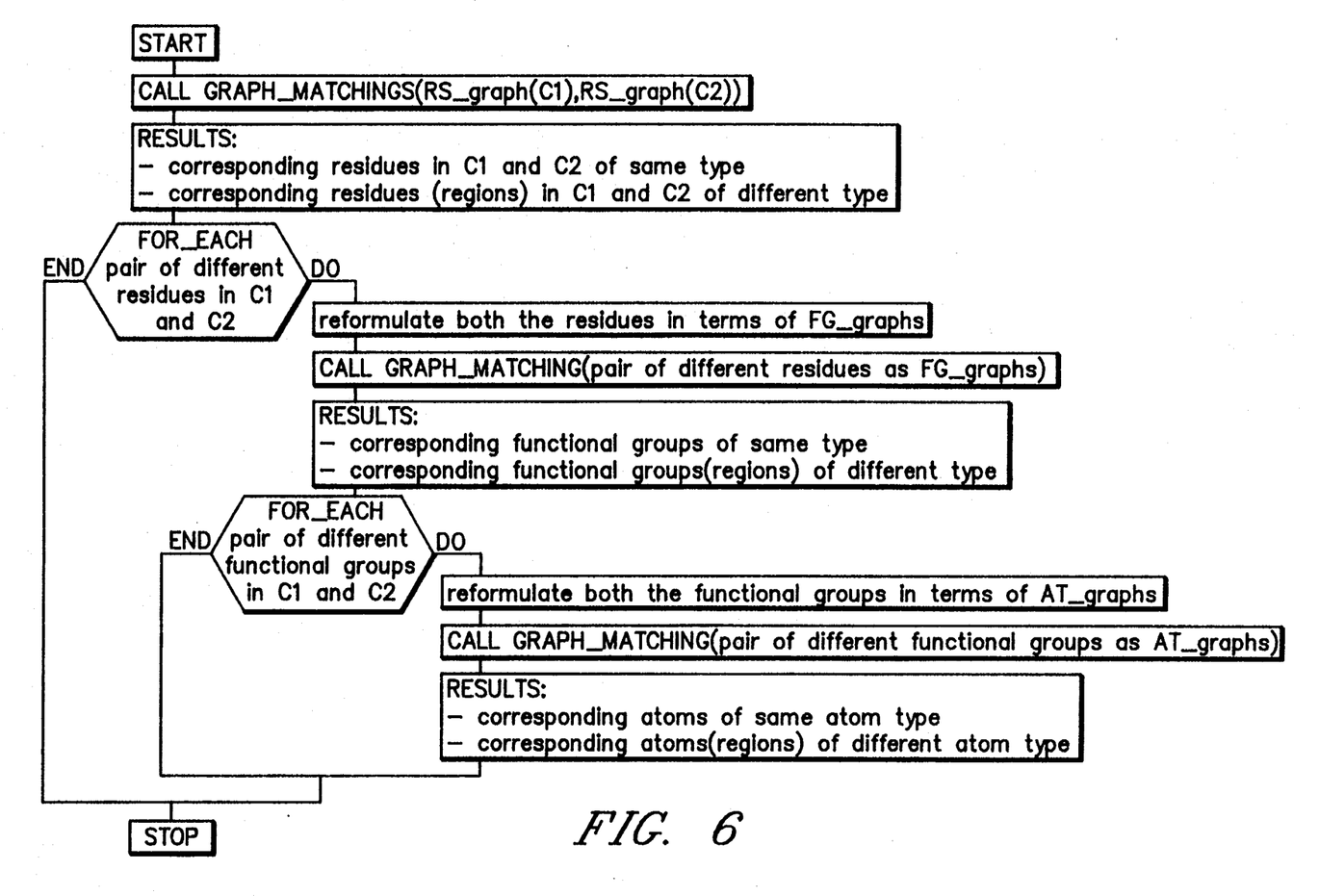
FIG. 6 is a flow chart of the structural matching routine.

1. Query for molecules structurally similar to an input one. The similarity is established through the maximum number of atoms allowed to form the difference. The end user can also require in the query that the difference must be from 1 up to N connected regions anywhere located. For this query type, module 5 activates fragment recognizer module 21 to analyze the input molecule so as to represent it in the hierarchical way described above, in connection with FIG. 3. The RS-graph and the FG-graph are generated in order to be associated with the representation of the input molecule (the AT-graph). Then, query analyzer module 25 calls structural matching module 26 to match the hierarchical description of the input molecule against the ones of the molecules stored into target database 23. The analysis of the query carried out from query analyzer 25 reduces the complexity of the matching procedure. Let us suppose, for instance, that the user is interested in molecules different from the input one only because of one region. Then module 26, during the matching process, will discard all the molecules that have more than one residue different with respect to the input molecule whenever such residues do not make a connected region. In this way, a high-level matching accomplished at the residue level will be sufficient to discard a great number of molecules useless for answering to the query under consideration. Specifically, structural matching module 26 takes as input two molecules or compounds C1 and C2 both represented at the same hierarchical level previously described and produces as output an association, whenever it exists, among the nodes of C1 and C2. Table 4 details the functioning of the structural matching routine. FIG. 6 is a flow chart of the operation of the structural matching routine. In its operation, module 26 recursively calls graph matching module 29 in order to firstly match the RS-graphs, then the FG-graphs and finally the AT-graphs. Graph matching module 29 takes as input two graphs G1 and G2 in which each node is identified by a label, such as, for instance, H1, and a type such as, for instance, H and each arc is identified by a pair of node labels, such as, for instance, arc(H1, H2). In this formalism, H1 must be understood as an instance of H. The output is an association, whenever it exists, of the nodes of the same type in G1 and G2 and the set of different nodes (regions) in G1 and G2. Specifically the graph

TABLE 4

The structural matching routine

1. CALL_GRAPH MATCHING (RS-graph of C1, RS-graph of C2).
   RESULTS:
       *a set of corresponding residues in C1 and C2
       identified as of the same type;
       *a set of corresponding different residues in C1
       and C2, identified as of different types.
2. FOR_EACH pair of different residues in C1 and C2:
   a. reformulate both the residues in terms of FG-graphs
      using the description of C1 and C2;
   b. CALL GRAPH_MATCHING (single difference in C1 and C2 in
      terms of FG-graphs).
      RESULTS:
          *a set of corresponding functional groups in
          these parts of C1 and C2 identified as of the
          same type;
          *a set of corresponding different functional
          groups in these parts of C1 and C2, identified
          as of different types.
   c. FOR_EACH pair of different functional groups C1 and C2:
      1) reformulate both the functional groups in terms of
         AT-graphs using the description of C1 and C2;
      2) CALL GRAPH_MATCHING (single difference in C1 and C2
         in terms of AT-graphs).
         RESULTS:
             *a set of corresponding atom types in
             these parts of C1 and C2;
             *a set of corresponding different atom

TABLE 4-continued

The structural matching routine types in these parts of C1 and C2.

matching subroutine makes use of the notion of "arc" as the matching elementary unit where an arc of G1 can be matched onto an arc of G2 widen the corresponding terminal nodes are of the same type.

Table 5 details the graph matching subroutine.

TABLE 5

The graph matching subroutine

1. DETERMINE the degree of each node. The degree of a node X is the number of arcs containing X as a terminal node.
2. CONSIDER a node N1 in the graph G1 with the maximal degree.
3. FIND into the graph G2 a node N2 of the same type of N1 and maximal degree. STORE in the matching_list the pair (N1, N2).
4. FOR_EACH arc in G1 containing N1, FIND a corresponding arc in G2 containing N2. IF the terminal nodes of the two arcs in G1 and G2 are of the same type, THEN STORE the new matched pair of nodes into the matching_list and delete the arcs from G1 and G2.
5. FOR_EACH new pair of matched nodes (N1, N2), recursively FIND a matching for all the new arcs containing N1 and N2: GOTO 4.
6. WHEN a connected region of arcs of G1 is maximally matched onto G2 (no more matching arcs can be found in the step 4 and 5), THEN GOTO 2 (the graph G1 and G2 are now reduced by the already matched arcs).
7. WHEN no more arcs in G1 and G2 are matchable, THEN FIND_ALL the connected regions of unmatched arcs in G1 and G2 and DETERMINE a matching between each unmatched region of G1 and each unmatched region of G2.

Figure 5:
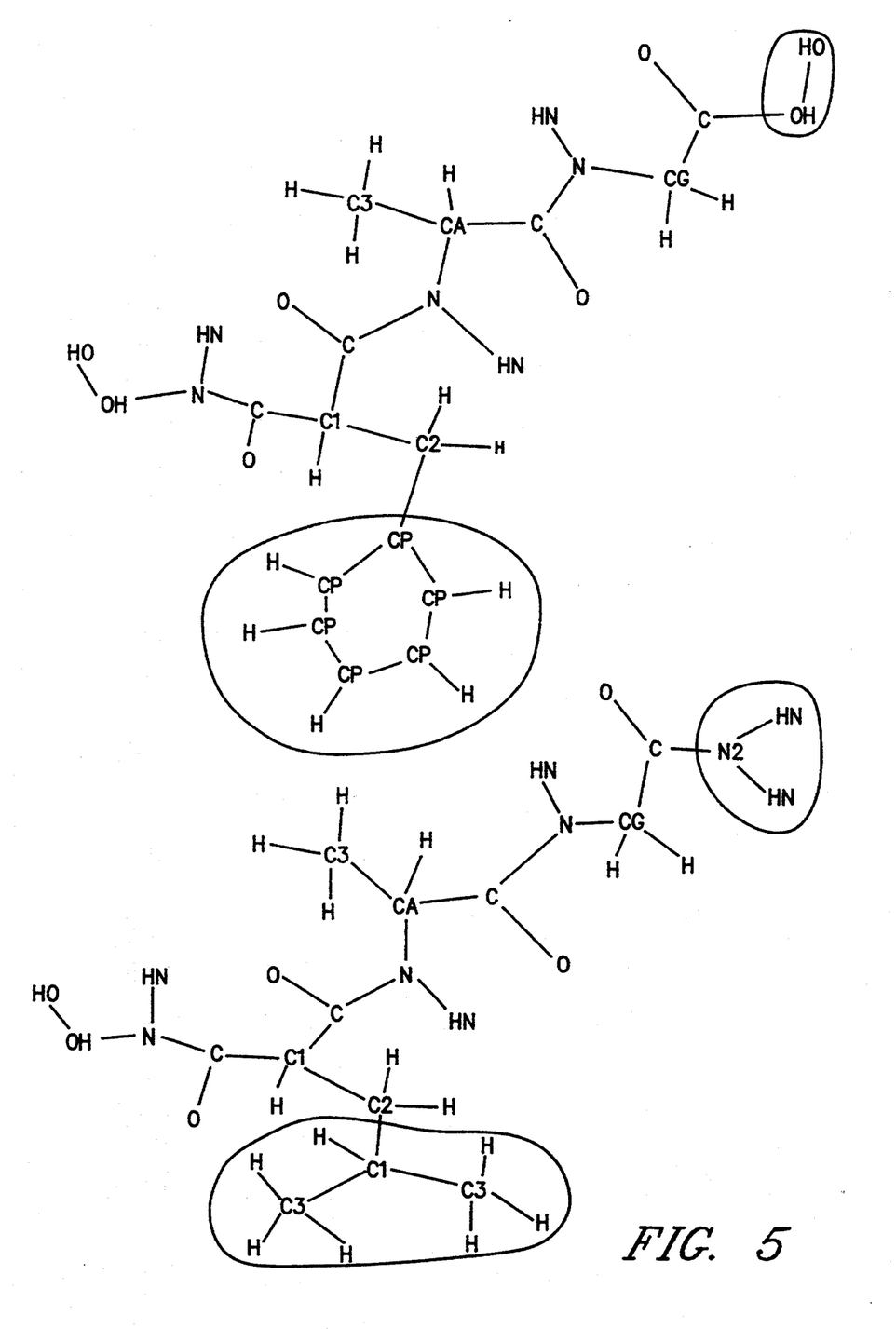
FIG. 5 shows the result of the partial matching as accomplished by the graph matching module between two molecules.

FIG. 5 illustrates the output of a call to the graph matching subroutine. The fragments circled highlight the uncommon regions between the input molecule and a structurally similar one.

An extension to the query type described above involves searching for pairs of molecules with minimal difference with respect to their structures and maximal difference with respect to any given property. Such a query is very useful when dealing with the Structure Activity Relationship problem in order to locate those fragments responsible for a major increase of the desired activity. The user is supposed to start his/her search from a subset of the molecules stored into target database 23 by using one of the query types here described. At this point, query analyzer module 25 calls structural matching module 26 to select all the pairs into such a subset that have the highest difference with respect to the required property and differ in only one residue (the activity value with respect to the given property is considered a property of the molecule as a whole as, for instance, the molecular weight). Whenever such molecules have been identified, structural matching module 26 will recursively call itself in the attempt at reformulating such a difference in terms of functional groups. Yet, the reformulation step will be accomplished only when satisfied the condition that the functional groups that actually make the difference also make a connected region. The same holds as concerns the functional group level. In this case, when the difference is expressed in terms of at most one functional group, module 26 again will recursively call itself in order to reformulate such a difference in terms of atom types on the condition above quoted.

2. Query for molecules containing a given property region, i.e. a substructure of the molecule that verifies a user defined combination of chemical and physical properties. Such a query, for instance, could ask for all the molecules that include a hydrophobic region with a volume greater than 20 cubic centimeters/mole and lesser than 40 cubic centimeters/mole. Firstly, query analyzer 25 looks into each of the dictionaries of the knowledge base 24 in order to select those fragments (residues functional groups atom types) that satisfy the user defined combination of chemical and physical properties. Following completion of this step, module 25 calls the structural matching module 26 to search in target database 23 for all the molecules including one of such fragments. Whenever volume is recognized as one of the properties used to define the region, query analyzer 25 will generate all the combinations of the fragments previously selected in order to identify those that fall into the range of the query. If the number of solutions is not too large, structural matching module 26 will search in target database 23 for all the molecules including one of the fragments or combinations of them previously selected. Otherwise, when the number of solutions is too large, query analyzer 25 will call model matching module 27 to search in target database 23 for all the molecules satisfying the user query (see below).

3. Query for molecules matching a user defined model represented in terms of fragments (namely: residues, functional groups, atom types) and/or property regions. Specifically, a model M is represented as a graph-whose nodes can be:
* residues,
* functional groups,
* atom types,
* property regions.

Figure 4:
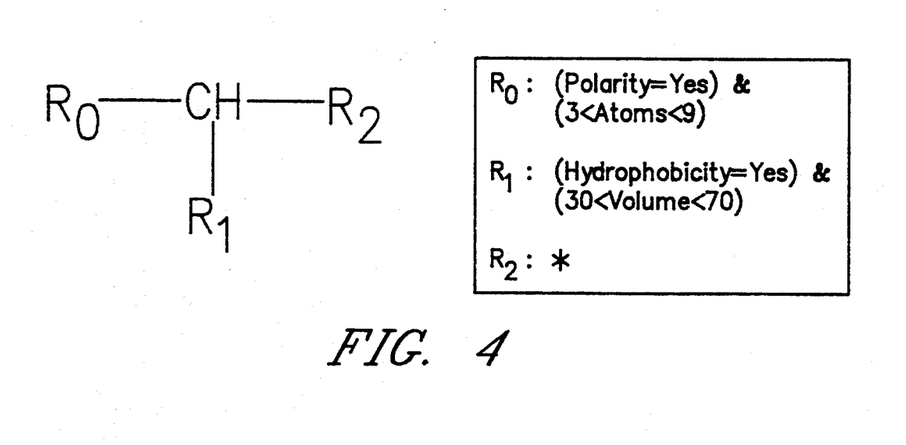
FIG. 4 shows an example of user defined model.
Figure 7:
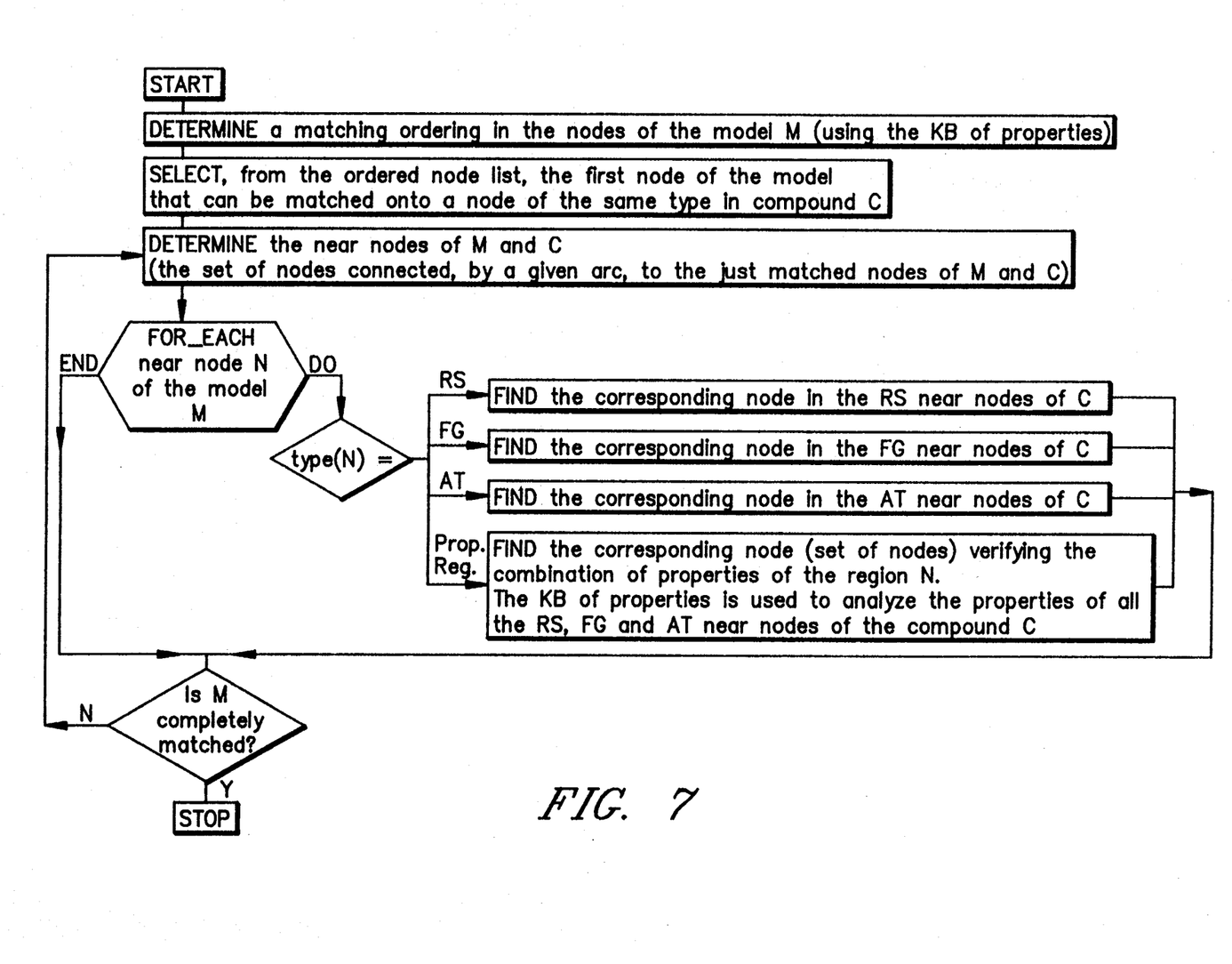
FIG. 7 is a flow chart of the model matching routine.

FIG. 4 illustrates an example of user defined model. Each Ri is a user defined property region with a number of properties associated to it. The '*' symbol stands for whatever fragment. The user is also allowed to define a measure of distance between subunits of the molecule in terms of number of bonds. Such a measure can span over a user defined interval. The task of model matching module 27 is to find an association, whenever it exists, between the nodes of the model M and the nodes of the compound C selected from target database 23 by query analyzer 25. Specifically, each node of the model M is selected in a preferred order (firstly residues, secondly functional groups, then atom types, finally property regions) in order to be matched onto the corresponding node of the compound C. Model matching module 27 takes as input the model M and the compound C represented in the hierarchical way previously described and produces as output an association, whenever it exists, among the nodes of the same type in M and in C. In order to match the property region nodes of the model M, module 27 calls knowledge base module 24 to check whether the corresponding fragment of the compound C verifies the properties appended at the node of the model M. Table 6 gives details about the model matching routine. FIG. 7 is a flow chart of the operation of the model matching routine.

TABLE 6

The model matching routine

1. FIND a RS-, FG- or AT-node of the model that can be matched onto a node of the same type in the compound C.
2. DETERMINE the near nodes of the model M and the compound C, that is the set of nodes that are connected, by a given arc, to the just matched nodes of the model and the compound. All the RS-, FG- and AT-graphs of the compound C are used in order to extract these near nodes.
3. FOR_EACH near node N of the model:
   *IF N is a residue node, THEN FIND the corresponding near node in the RS near nodes of the compound C.
   *IF N is a functional group node, THEN FIND the corresponding near node in the FG near nodes of the compound C.
   *IF N is an atom type node, THEN FIND the corresponding near node in the AT near nodes of the compound C.
   *IF N is a property region node, THEN FIND in all the RS, FG and AT near nodes of the compound C a node (or a set of nodes) that verifies the properties characterizing the property region N. In this case, the KB of chemical and physical properties is consulted in order to analyze the properties of the nodes of the compound C.
4. IF the model M is not completely matched, THEN GOTO step 2.

For all the query types previously described, the answer to the query is dispatched by query analyzer 25 to user interface 28.

The invention was described with no reference to a specific computer language; therefore, it will be understood that it can be implemented in any computer language.

We claim:

1. A molecular retrieval method for retrieving molecular structures, stored in a molecular database and having similarity with an input reference, comprising the steps of:
   (a) defining a hierarchy of molecular representations at residue, function group, and atom type structural levels;
   (b) identifying molecular fragments at each structural level of step a) and building a dictionary of said molecular fragments for each structural level;
   (c) collecting the chemical and physical properties for each molecular fragment of said dictionaries and building a knowledge base;
   (d) selecting a structual level of molecular representation on the basis of similarity to said input reference;
   (e) performing a matching between the representation of said input reference against the molecular representations at the level selected in step d) of all the molecular structures stored into said molecular database using said knowledge base;
   (f) selecting all the molecular structures similar to said input reference, and outputting all the molecular structures selected in step f).

2. The molecular retrieval method of claim 1 wherein said input reference is an input molecule and the matching of step (e) comprises:
   (i) performing a first matching between a first structural level of said input molecule against the same structual level of the molecular database; and
   (ii) performing a second matching at the next lower structual level between the different molecular fragments, discovered in said first matching, of said input molecule and the molecular structures stored into said molecular database and represented at the same level.

3. The molecular retrieval method of claim 1 wherein the input reference is a molecular model, represented as a graph with nodes selected from property regions and molecular fragments, and the matching of step (e) comprises
   (i) defining a property region, as any molecular fragment that matches a user defined combination of chemical and physical properties;
   (ii) identifying an ordering in the nodes of said molecular model, using said knowledge base; and
   (iii) performing matching between each node of said model and all the molecular structures stored into said molecular database, using said knowledge base.

4. A molecular retrieval system for retrieving molecular structures, stored into a database and having a required similarity with an input reference comprising:
   (a) a first storage means for storing a hierarchical description of said molecular structures as molecular fragments in different structual levels;
   (b) a second storage means for storing known molecular fragments at different structual levels and for storing a set of physical and chemical properties associated to each of said fragments;
   (c) a recognizing means for recognizing the fragments appearing in the input reference so as to represent them in a hierarchical description;

(d) an analyzing means for a selecting a structual level of hierarchical description of molecular structures on the basis of similarity to said input reference;

(e) a matching means that, when called by said analyzing means, performs a matching of the fragments of said input reference against the fragments of the molecular structures stored into said first storage means at the said structual level.

5. The molecular retrieval system of claim 4 wherein said input reference is a molecular structure.

6. The molecular retrieval system of claim 4 wherein said input reference is a user defined molecular model.

* * * * *